US009925210B2

(12) United States Patent
McCarthy et al.

(10) Patent No.: US 9,925,210 B2
(45) Date of Patent: Mar. 27, 2018

(54) CHITOSAN MATERIALS FROM CARBONIC ACID SOLUTION

(71) Applicant: Tricol Biomedical, Inc., Portland, OR (US)

(72) Inventors: Simon McCarthy, Portland, OR (US); Barbara McGrath, Portland, OR (US); Sam Kuhn, Portland, OR (US); Jess Kimball, Portland, OR (US); Michael Stolten, New Orleans, LA (US); Amanda Bennett, New Orleans, LA (US)

(73) Assignee: Tricol Biomedical, Inc., Portland, OR (US)

(*) Notice: Subject to any disclaimer, the term of this patent is extended or adjusted under 35 U.S.C. 154(b) by 0 days.

(21) Appl. No.: 14/614,316

(22) Filed: Feb. 4, 2015

(65) Prior Publication Data

US 2015/0216894 A1 Aug. 6, 2015

Related U.S. Application Data

(60) Provisional application No. 61/935,569, filed on Feb. 4, 2014.

(51) Int. Cl.
| | | |
|---|---|---|
| *A61K 31/722* | (2006.01) | |
| *A61K 9/19* | (2006.01) | |
| *A61K 9/16* | (2006.01) | |
| *A61K 47/12* | (2006.01) | |
| *A61K 9/70* | (2006.01) | |

(52) U.S. Cl.
CPC .......... *A61K 31/722* (2013.01); *A61K 9/1652* (2013.01); *A61K 9/1694* (2013.01); *A61K 9/19* (2013.01); *A61K 9/70* (2013.01); *A61K 47/12* (2013.01)

(58) Field of Classification Search
CPC ..... A61K 31/722; A61K 47/12; A61K 9/1652
See application file for complete search history.

(56) References Cited

U.S. PATENT DOCUMENTS

| | | | | |
|---|---|---|---|---|
| 7,371,403 | B2* | 5/2008 | McCarthy ........... | A61F 13/0203 424/445 |
| 2005/0196497 | A1* | 9/2005 | Soedjak ................... | A23L 2/02 426/324 |
| 2013/0164311 | A1 | 6/2013 | Decarlo et al. | |

FOREIGN PATENT DOCUMENTS

| | | |
|---|---|---|
| CA | 2134635 | 5/1995 |
| WO | WO 01/41820 | 6/2001 |

OTHER PUBLICATIONS

Shepherd et al., Glycoconjugate J., 1997, 14, p. 535-542.*
Gorczyca et al., Carbohydr. Polym., 2014, 102, p. 901-911, Available online Nov. 2, 2013.*
Gallyamov et al. Collagen tissue treated with chitosan solutions in carbonic acid for improved biological prosthetic heart valves. Materials Science and Engineering 127-140, Jan. 11, 2014. [ retrieved on Jun. 4, 2015]. Retrieved from the Internet. <URL: http://www.sciencedirect.com/science/article/pii/S0928493114000186>.
Berscht et al., "In vitro evaluation of biocompatibility of different wound dressing materials," Journal of Materials Science: Materials in Medicine, Germany; 201-205 (1995).
Butler et al., "Carbon dioxide equilibria and their applications," Lewis Publishers, Michigan; 1-73 (1991).
Cafaggi et al., "Preparation and evaluation of chitosan salt-poloxamer 407 based matrix for buccal drug delivery," Journal of Controlled Release, Italy; 159-169 (2005).
Grabovac et al., "Comparison of the mucoadhesive properties of various polymers," Advanced Drug Delivery Reviews, Austria; 1713-1723 (2005).
He et al., "Preparation of chitosan films using different neutralizing solutions to improve endothelial cell compatibility," Springer Science+Business Media, LLC, China; 2791-2802 (2011).
Hobbs et al., "Ice physics," Oxford University Press, London; 575-629 (1974).
Johnson et al., "In vito tissue response to implanted chitosan glutamate," Advances in Chitin and Chitosan, Minnesota; 3-8 (1991).
Lee et al., "Synthesis and characterization of a chitosan derivative," Harvey Mudd College, California; 1-2 (2013).
MacKenzie, A.P. "The physico-chemical basis for the freeze-drying process," Develop. boil. Standard, Basel: 51-67 (1976/1997).
Miya et al., "I.r. spectroscopic determination of CONH content in highly deacylated chitosan," IPC Business Press, Japan; 323-324 (1980).
"Electrical conductivity of aqueous solutions," CRC Handbook of Chemistry, and Physics, 70th Edition, CRC Press, Florida; D-221 (1989).
Sakai et al., "A novel method of dissolving chitosan in water for industrial application," Polymer Journal, Japan; 640-642 (2001).

(Continued)

*Primary Examiner* — Jonathan S Lau
(74) *Attorney, Agent, or Firm* — Seed IP Law Group LLP; Chandra E. Eidt

(57) ABSTRACT

The present invention comprises chitosan materials and methods of using carbonic acid for aqueous solubilization of neutralized or pre-treated chitosan gels and provides, among other things, substantially acid salt free composition native final forms without requiring subsequent acid salt elution. The invention includes chitosan-based solid and semi-solid material forms, optionally reinforced with chitosan fibers, such as powders, fibers, films, matrices, sponges, implants, scaffolds, fillers, and hydrogels. Native final forms are produced from chitosan powder solubilized in an aqueous acidic solution, processed to form a high pH hydrated chitosan gel precipitate material that is then neutralized by water washing and re-solubilized substantially to chitosan solution using carbonic acid. Chitosan materials can be mixed in solution with one or more of other hydrophilic polymers to create compositional heterogeneity and pharmaceutical agents to achieve controlled release of the agent(s) from the final forms at the site of application.

12 Claims, 6 Drawing Sheets

(56) References Cited

OTHER PUBLICATIONS

Sakai et al., "Chitosan-coating of cellulosic materials using an acqueous chitosan-CO2 solution," Polymer Journal, Japan; 144-148 (2002).
Sigurdsson et al., "Assessment of mucoadhesion by a resonant mirror biosensor," International Journal of Pharmaceutics, Germany; 75-81 (2006).
Tang et al., "Antibacterial action of a novel functionalized chitosan-arginine against Gram-negative bacteria," Acta Biomaterialia, United States; 2562-2571 (2010).
"Carbonic Acid," Wikipedia; <"http://en.wikipedia.org/w/index.php?title=Carbonic_acid&oldid=643507228"> Last modified Jan. 21, 2015.

* cited by examiner

CHITOSAN MATERIALS FROM CARBONIC ACID SOLUTION

RELATED APPLICATIONS

This application claims priority to U.S. provisional patent application Ser. No. 61/935,569 filed on Feb. 4, 2014, the contents of which are fully incorporated herein by reference.

STATEMENT REGARDING FEDERALLY SPONSORED RESEARCH OR DEVELOPMENT

This invention was made with government support under Contract Award W81XWH-08 2-0120 awarded by U.S. Army Medical Materiel Development Activity. The government has certain rights in the invention.

INVENTION SUMMARY

The present invention relates to unique chitosan materials and methods for their production that use carbonic acid for aqueous chitosan solubilization and result in, among other things, composition native final forms that are substantially acid salt free when brought into final form and that do not require acid salt elution. The term "native final form(s)" as used with the present invention comprises both solid and semi-solid finished compositions derived from chitosan carbonic acid solution. Solid native final forms are dried (including temperatures≤0° C.) to include ≤70% w/w water and can be subsequently washed with de-ionized water without substantial change in water conductivity, indicating absence of salt impurity. Alternatively, semi-solid native final forms, such as hydrogels, remain hydrated to include ≥70% w/w water.

Regardless of water content, native chitosan based material final forms such as powders, fibers, films, matrices, sponges, implants, scaffolds, fillers, and hydrogels are produced from chitosan powder that has been i) solubilized in an aqueous acidic solution (<pH 6.5), ii) processed to form a high pH (≥pH 10.0) hydrated chitosan gel precipitate material, that is then iii) neutralized (i.e., has safe physiological pH of ≥about 5.0 and ≤about 8.5) by washing in water and/or otherwise pre-conditioned, and iv) subsequently re-solubilized substantially to chitosan carbonic acid solution directly from the washed hydrated gel precipitate using carbonic acid as received or formed from application of partial pressure of carbon dioxide to water.

In some embodiments, these native chitosan based materials final forms can include hydrophilic polymers to create final forms with polymeric compositional heterogeneity. The hydrophilic polymers can be mixed in with the chitosan carbonic acid solution.

In some embodiments, these native chitosan based materials final forms can include one or more pharmaceutical active agents to achieve controlled release of the active(s) from final forms at the site of application. The one or more pharmaceutical active agents can be mixed in with the chitosan carbonic acid solution. Alternatively, the one or more pharmaceutical active agents may be impregnated into the final forms for controlled release at the site of application.

In some embodiments, the application of shear and freeze phase separation are used to make final forms with complex structures directly from the chitosan carbonic acid solution. Surprisingly, these final forms resist dissolution when re-exposed to the original solvent.

In some embodiments, additional processes such as shear and freeze phase separation may be used to dehydrate some or all of the chitosan in the chitosan carbonic acid solution to make it resist dissolution in carbonic acid.

In some embodiments, additional partial pressure of carbon dioxide in the carbonic acid chitosan solution may be adjusted between around pH 3.4 at 10 atmospheres of carbon dioxide pressure to pH 7.0 with no carbon dioxide pressure. See Butler, J. N., *Carbon dioxide equilibria and their applications*. 1991: Lewis Publishers, Chelsea, Mich. This capability allows for convenient adjustment of pHs to, for example, near about 7.0 in the case of introduction of pH sensitive molecules to the chitosan solution.

The chitosan composition final forms of the present invention, which are substantially free of acid salts without need for acid salt elution in their native state or form, are highly desirable for certain medical applications. This is because the presence of acid salt in the chitosan composition adversely affects biocompatibility, removal of acid salt in the final chitosan forms by elution also removes included active agents, and presence of acid salt can also cause the chitosan composition to adhere strongly to wet tissue surfaces, making its subsequent removal difficult and potentially resulting in damage to the treated sensitive wet tissue surface.

Further, and advantageously, the inventors have determined that the chitosan composition native final forms of the present invention can be used in wound treatment, regenerative medicine, and drug delivery, and can be applied without significant change on wetting, can remain on wounds, or treated wet tissue surfaces, wetted over four to seven days without significant change, do not dissolve in water, saline, blood or other biological fluid, can be used to readily contain active pharmaceutical ingredients, can be used to achieve controlled release of pharmaceutical ingredients, or serve as drug delivery vehicles, conform readily to surfaces, can be easily removed, and can be removed intact (absence of tearing, fragmentation, or breaking into pieces).

BACKGROUND

Chitosan materials are typically produced using dilute aqueous solutions of acetic, hydrochloric, formic, glycolic, lactic, and other acids to readily dissolve and solubilize chitosan powder. Conventionally, this chitosan powder solubilized in acidic solution is then directly used to produce chitosan material finished forms, and the acids used for chitosan powder solubilization continue to reside in and be part of the chitosan material finished forms absent further processing. All acids, including, but not limited to, acetic, lactic, hydrochloric, glycolic and glutamic acid, that solubilize chitosan in aqueous solution interact with chitosan to form an acid salt complex, wherein the cation moiety of the salt complex is a positively charged glucosammonium of the chitosan and the anion counter-ion negatively charged moiety is provided from the anion of the added acid. The formation of this acid salt complex is the reason that chitosan becomes solubilized in water at about pH≤6.5. On removal of the water from the chitosan acidic solution, the salt complex substantially remains, i.e., at a presence of ≥about 5.0% w/w in the chitosan affecting its biocompatibility and its bioactivity.

Deleterious secondary or post-processing of the chitosan material finished forms is required to remove or extract the resident acid in order to achieve, among other things, non-adherent chitosan finished forms and to mitigate the adverse effects that unwanted acid presence can have on biocompatibility. See Berscht, P. C., Nies, B., Liebendorfer, A., and Kreuter, J., *In Vitro evaluation of biocompatibility of different wound dressing materials*, JOURNAL OF MATERIALS SCIENCE: MATERIALS IN MEDICINE, 1995, 6: p. 201-205 ("Berscht"); Johnson, R. S., Lewis, T. W., and Lampecht, E. G., *In vivo tissue response to implanted chitosan glutamate*, ADVANCES IN CHITIN AND CHITOSAN, C. J. Brine, P. Sandford, and J. P. Zikakis, Editors. 1992, Elsevier: Amsterdam. p. 3-8 ("Johnson"); Cafaggi, S., Leardi, R., Parodi, B., Caviglioli, G., Russo, E., and Bignardi, G., *Preparation and evaluation of a chitosan salt-poloxamer 407 based matrix for buccal drug delivery*, JOURNAL OF CONTROLLED RELEASE, 2005. 102(1): p. 159-169 ("Cafaggi"); Grabovac, V., Guggi, D., and Bernkop-Schnürch, A., *Comparison of the mucoadhesive properties of various polymers*, ADVANCED DRUG DELIVERY REVIEWS, 2005. 57(11): p. 1713-1723 ("Grabovac"); Sigurdsson, H. H., Loftsson, T., and Lehr, C.-M., *Assessment of mucoadhesion by a resonant mirror biosensor*, INTERNATIONAL JOURNAL OF PHARMACEUTICS, 2006. 325(1-2): p. 75-81 ("Sigurdsson"); He, Q., Ao, Q., Gong, Y., and Zhang, X., *Preparation of chitosan films using different neutralizing solutions to improve endothelial cell compatibility*, JOURNAL OF MATERIALS SCIENCE: MATERIALS IN MEDICINE, 2011, 22(12): p. 2791-2802 ("He").

Further, the acid-removal processing of conventional chitosan material finished forms involves solvent extraction or other harsh processes and undesirably and negatively alters the chitosan material finished form properties including its shape, structure, capacity for viable drug stability, retention, and delivery, porosity, morphology, and other mechanical properties. Additional post-processing acid removal steps also add further difficulty, complications, and costs to the manufacture of conventional chitosan material finished forms.

The present invention addresses a long-standing need in the art to produce chitosan material native final forms that are substantially free of acid salts upon their production, i.e., no subsequent and additional processing steps are required to remove resident acids from the chitosan material finished forms. Surprisingly, the inventors of the present invention not only found a solution to this long-standing problem, but have also discovered and developed robust and unique chitosan material native final forms that, unlike prior art chitosan material finished forms, can be applied without significant change on wetting, can remain on wounds, or treated wet tissue surfaces, wetted over four to seven days without significant change, do not dissolve in water, saline, blood or other biological fluid, can be used to readily contain active pharmaceutical ingredients, can be used to achieve controlled release of pharmaceutical ingredients, can be molded as hydrogels to designed shape, can achieve remarkable fluid absorbency while substantially retaining their overall shape dimensions, or serve as drug delivery vehicles, conform readily to surfaces, can be easily removed, and/or can be removed intact (with absence of tearing, fragmentation, or breaking into pieces).

DETAILED DESCRIPTION

The native chitosan material final forms and processes of production of the present invention represent several departures from the prior art, including the use of carbonic acid to produce chitosan composition final forms substantially free of acid salt.

Semi-solid and solid dried native chitosan material final forms are considered to be "substantially free of acid salt" when they contain ≤about 5% (w/w) acid salt, preferably ≤about 1% (w/w) acid salt, more preferably ≤about 0.1% (w/w) acid salt, and most preferably ≤about 0.01% (w/w) acid salt.

In one embodiment, pure, dried carbonic acid chitosan final forms (e.g., about 0.07 g) substantially free of acid salt may be dried and/or freeze phase-separated from chitosan carbonic acid solution at temperatures ≤0.0° C., or dried at temperatures >0.0° C. These dried carbonic acid chitosan final forms are then washed in deionized water (e.g., about 5.0 g) at 23±2° C. (conductivity≤0.5 microsiemens/cm) such that conductivity difference between the washing and control deionized water is ≤1.5 microsiemens/cm at ≤1 hour of washing.

The embodiments described herein address the use of a clean and safe acid, carbonic acid, that may be used to solubilize a neutralized or pre-conditioned hydrated chitosan gel as part of a chitosan carbonic acid solution and allows for drying and formation of final forms that are either solid and semi-solid without leaving substantial residue (i.e., salt≤1.0% w/w or pH≤8.0) of acid salt.

Ions at homeostatic electrolyte (isotonic) concentration may be added during the pre-conditioning washing step by using washing aqueous solutions of ions adjusted to desirable physiological levels. Examples of such ions and their concentrations may include, but are not limited to, sodium chloride about 0.9% w/w in water; and phosphate buffered saline with sodium chloride about 0.8% w/w, potassium chloride about 0.02% w/w, disodium phosphate about 0.144% w/w, and monopotassium phosphate about 0.024%.

Importantly, once the native chitosan material final forms are formed as solid or semi-solid, they do not re-dissolve in the same acid solution which dissolved the originally neutralized or pre-conditioned gel.

The term "semi-solid" is indicated here to describe phase separated hydrogel native chitosan material final forms, such as from aqueous freeze phase-separated chitosan or shear phase separated chitosan. Such hydrogel native chitosan material final forms remain substantially hydrated in the presence of water but are insoluble in the acid solution used to dissolve the neutralized or pre-conditioned chitosan gel.

The term "neutralized or pre-conditioned hydrated chitosan gel" is indicated here to describe hydrated gel (i.e., a gel which can be redissolved) comprising ≥about 95% w/w water which is formed by dissolution of chitosan directly from substantially dehydrated gel (intractable gel; hydrogel) (≤70% w/w water) chitosan powder or a similar chitosan solid by dissolution in an acid which may include, but is not limited to, formic, acetic, lactic, glycolic, hydrochloric and glutamic acids. The acid used to dissolve the chitosan powder or similar chitosan solid is subsequently neutralized to pH≥about 7 by addition of excess base (preferably to pH≥about 10) which base may include, but is not limited to, ammonia, sodium hydroxide and potassium hydroxide. The resultant toxic high pH and high salt content hydrated aqueous chitosan gel is washed with water solutions to neutralize the gel by substantially reducing its pH to safe physiological levels (8.5≥pH≥5.0) and/or adjusting the ionic salt concentration to physiologically safe levels. Physiologically safe levels of salt are preferably ≤3.5% w/w of a salt solution, more preferably they are ≤2.0% w/w salt solution and most preferably they are ≤1.0% w/w salt solution.

For example, a preferred safe salt concentration may be obtained by washing with pure water to substantially remove all the salt in the pre-conditioned hydrated chitosan gel. Salt concentrations are conveniently measured in aqueous salt solution using conductivity methods that sensitively measure the effect of the presence of mobile conductive ions on the electric current carrying capacity of water. Typically conductivity is measured at constant temperature and its International Standard (SI) unit of measurement is siemens/cm. At 20° C., absolute pure water has conductivity close to 0.05 microsiemens/cm. Very high quality rain water has conductivity close to 1.0 microsiemens/cm while seawater (3.0 to 3.5% salinity) has conductivity between 40,000-50,000 microsiemens. Conductivity has the ability to readily detect the presence of ions in water at parts per million or less.

Because carbonic acid does not dissolve chitosan powder in dilute aqueous solutions, dissolution of chitosan powder by carbonic acid requires that the chitosan be in an aqueous gel form. See Sakai, Y., Hayano, K., Yoshioka, H., Fujieda, T., Saito, K., and Yoshioka, H., *Chitosan-coating of cellulosic materials using an aqueous chitosan-CO2 solution*, POLYMER JOURNAL, 2002. 34(3): p. 144-148 ("Sakai 1"); Sakai, Y., Hayano, K., Yoshioka, H., and Yoshioka, H., *A novel method of dissolving chitosan in water for industrial application*, POLYMER JOURNAL, 2001. 33(8): p. 640-642 ("Sakai 2").

According to the present invention, and as a general matter, the aqueous gel form of chitosan is prepared by complete dissolution of the chitosan powder under dilute acid conditions (typical dilute acids may include, but are not limited to, acetic, glycolic, lactic, and hydrochloric acids) followed by sedimentation of an aqueous gel precipitate by raising the acid solution pH to ≥about 10.0 with a base (bases may include, but are limited to, potassium hydroxide, sodium hydroxide, ammonia, sodium carbonate and/or sodium bicarbonate). Then the chitosan gel precipitate is neutralized by washing in water.

Typically, the precipitated gel residue is in the form of gel particles about ≥0.25 mm or gel fibers about ≥0.5 mm length, which are contained in a permeable fine mesh bag or similar mechanical strainer in the washing step. Sedimentation of gel precipitate with decantation of substantially chitosan free liquid may be used as an alternative method of washing and collecting the precipitate after washing, or it may be used in combination with the strainer washing approach. Centrifugation may be used to accelerate separation of the precipitate from its aqueous wash. Such approaches all achieve the end result, which is removal of mobile and water soluble low molecular weight species from the immobile, high molecular weight, fully-hydrated chitosan gel precipitate by repeated washing. For medical or pharmacological applications, the neutralization and washing is preferably performed under suitable environmental controls such as International Organization for Standardization (ISO) Class 7 or less with the water used in the washings of high purity suitable for medical or parenteral use.

The washing step process is typically informed by determination of the conductivity or pH of final washings in the presence of the chitosan gel for about ≥4 hours. The target conductivity at 23±2° C. for the final washings in the washing step is preferably about ≤50 microsiemens/cm, more preferably about ≤10 microsiemens/cm and most preferably about ≤1 microsiemens/cm. Chitosan gels having a conductivity at 23±2° C. for the final washings in the washing step of preferably about ≤50 microsiemens/cm, more preferably about ≤10 microsiemens/cm and most preferably about ≤1 microsiemens/cm are considered "neutral" or "neutralized" for the purposes of the present invention. The target pH for the final washings in the washing step is a safe physiological pH of ≥about 5.0 and ≤about 8.5, preferably ≥about 5.5 and ≤about 8.0, more preferably ≥about 6.0 and ≤about 7.5, and most preferably about ≥about 6.5 and ≤about 7.0.

The washed hydrated chitosan gel precipitate may be referred to herein as a neutralized gel. Once the acid salt residues are removed from the hydrated gel precipitate or neutralized gel, the hydrated gel is then re-solubilized by acidification with the carbonic acid.

In one embodiment of the present invention, the preparation of the neutralized gel for re-dissolution with carbonic acid, may involve preparation of a substantially carbonic acid insoluble fibrous gel precipitate by shear induced mechanical dehydration of extruded, elongated chitosan gel, such that the carbonic acid dissolves the bulk of the gel without dissolution of the partially dehydrated chitosan fibers. Following the agitation and mixing applied for carbonic acid dissolution, the chitosan fibers may then remain uniformly dispersed and insoluble through the viscous solution (at 25° C. the solution/dispersion viscosity is generally about ≥100 cps) until processing to a final form. This dispersed chitosan fiber material in the chitosan solution may provide a milky/opaque appearance in dry and wet finished articles. Finished articles reinforced with this dispersed chitosan fiber material have improved wet handling properties compared to articles without the dispersed insoluble chitosan. Wet handling properties are important for matrices or dressing materials that either need to be wet when applied to wounds or become wet from wound exudate or blood after wound application.

The chitosan powder starting material is soluble at 1% w/w in 1% w/w acetic acid aqueous solution. It may include and is not limited to materials from shrimp, crab, squid, and or fungal sources. It is preferably of percentage degree of deacetylation from 15% to 100%, more preferably from 78% to 98% and most preferably from 85% to 98%. The number average molecular weight is preferably from 1 to 500,000 kda, more preferably from 10 to 1,000 kda and most preferably 50 to 300 kda.

The present invention involves the use of volatile carbonic acid to re-solubilize a neutralized, washed chitosan gel. The carbonic acid concentration may be controlled by partial pressure of carbon dioxide in the solution. Substantially acid free finished chitosan articles may be formed by freeze-phase separation at temperature below 0.0° C., by lyophilization drying (at temperature below 0.0° C.) and by casting, sputtering, spraying and spinning processes with thermal drying at temperatures above 0.0° C. Freeze phase separation in the case of aqueous solution is caused by local nucleation of pure ice microdomains with their subsequent growth causing formation of microdomains containing all of the non-aqueous component (now insoluble in the ice) which was originally solubilized in the water. See Hobbs, P. V., Ice Physics. 1974, New York: Oxford Univ. Press ("Hobbs").

The resultant native chitosan material finished forms may comprise a chitosan powder, fiber, film, matrices, sponges, implants, scaffolds, fillers, and hydrogels that contain no, or substantially no, residual acid salt. The resultant chitosan material finished forms do not require secondary treatment to remove residual acid since none, or substantially none, is present. Pure, dried carbonic acid chitosan forms (e.g., about 0.07 g) substantially free of residual acid salt may be dried and/or phase separated from solution at temperatures≤0.0° C.; or dried at temperatures>0.0° C. and then washed in deionized water (e.g., about 5.0 g) at 23±2° C. (conductivity≤0.5 microsiemens/cm) such that the conductivity difference between washing and control deionized water is ≤1.5 microsiemens/cm at ≤1 hour of washing.

Re-solubilized chitosan carbonic acid solutions can range from about 0.1% w/w chitosan to about 7% w/w chitosan, and preferably range from about 0.5% w/w chitosan to about 2.5% w/w chitosan.

In one embodiment, the re-solubilized chitosan carbonic acid solutions may be processed into finished films, powders, or fibers by casting or spraying through a CO2 depleted fluid or gas and/or onto surfaces with application of heat.

In another embodiment, the chitosan carbonic acid solutions typically ranging from about 0.1% w/w chitosan to about 7% w/w chitosan, and preferably from about 0.5% w/w chitosan to about 2.5% w/w chitosan, may be processed into finished 3-dimensionally printed scaffolds/matrices by pulse spraying, pulse depositing or pulse injecting droplets of the solution under pressure through a movable directed small diameter, or similar small dimension profile nozzle. After leaving the nozzle, the droplets may pass through a CO2 depleted fluid or gas before being collected at their targeted accumulating surface profile.

To effect drying, heat may be applied over the accumulating body of the 3-dimensional construct either conductively, radiantly, or by convective means. Dispersed reinforcing additives may be included into the carbonic acid chitosan droplet. These may include, but are not limited to, hydroxyapatite, carbon nanotubes, clays, graphene, metals and metal oxides.

In another embodiment, the chitosan carbonic acid solutions typically ranging from about 0.1% w/w chitosan to about 7% w/w chitosan, may be processed into finished fiber by continuous extrusion under shear through a fine diameter, or similar small dimension profile nozzle. After leaving the nozzle, the continuous fiber may pass through a CO2 depleted fluid or gas before being collected at a surface. Heat may be applied to promote drying of the fiber either conductively, radiantly, or by convective means.

In another embodiment, chitosan porous sponge, scaffold, or matrices native chitosan material finished forms are produced by freeze-phase separation of the re-solubilized chitosan carbonic acid solution into lamella domains of chitosan and ice by application of gradient cooling over ≥60 seconds with base temperature maintained at less than −20° C., initial solution temperature above 0.0° C. and sponge/matrix/scaffold thickness of about ≥0.25 mm. The resultant partially dehydrated freeze phase-separated structure retains its structure on melting/thawing of the ice providing for a novel pure, highly water absorptive chitosan structure, which is substantially free of acid salt and which is insoluble in water and in carbonic acid. Typically, absent the present invention, such chitosan freeze phase-separated structures can only be retained by freeze-drying (sublimation) removal of the ice since re-exposure of the phase separated chitosan to its thawed aqueous acid (its original solvent) causes dissolution and structure collapse. Dispersed reinforcing additives may be included into the carbonic acid chitosan solution prior to freeze phase separation. These may include, but are not limited to, hydroxyapatite, carbon nanotubes, clays, graphene, metals and metal oxides.

Surprisingly, and advantageously, the chitosan carbonic acid solution approach of the present invention provides a means to quickly and efficiently produce and maintain complex porous chitosan structure from aqueous chitosan carbonic acid solution using freeze phase separation or 3-dimensional printing approaches without the need for freeze-drying and/or without the need for secondary treatment steps to remove residual acids.

Avoiding the conventional requirement of freeze-drying to preserve complex porous chitosan structure, such as in the case of the freeze phase-separated native chitosan material finished forms, provides a substantial and important improvement over the prior art. This freeze phase-separation ability, without need for freeze-drying, is highly advantageous as it offers a mean to inexpensively and effectively produce low density (e.g., about 0.005-0.25 $g/cm^3$), porous based matrix, scaffold, sponge, and hydrogel structures in a continuous fashion and eliminates time consuming and expensive step of freeze-drying.

Freeze-dryers used to produced medical products typically cost hundreds of thousands and sometimes millions of dollars ($USD) to install, produce material over days in single batches, and are similarly costly to maintain. Products produced by freeze-drying typically can be at least an order of magnitude (×10) more expensive than products produced by a continuous processing approach. Other than by freeze solvent extraction (itself a problematic technique), no other methods have been previously described which allow for achieving and preserving the unique structure typically offered by freeze phase separation without use of freeze-freeze-dryingdrying.

Because of its high level of aqueous absorbency (near 1000% w/w) carbonic acid chitosan freeze-phase separated native chitosan material finished forms may be used in a manner similar to a hydrogel product when its water is retained. Alternatively, it may be processed using drying steps other than freeze-drying. Such drying steps are generally more efficient than freeze-drying and may include, but are not limited to, mechanical compression and/or adsorptive padding. Application of heat may also be used. These steps may include, but are not limited to, application of heat by conduction, radiant energy and convective means. Drying of the final chitosan article is intended to reduce water to ≤about 70% w/w, preferably ≤about 10% w/w; more preferably ≤about 5% w/w and most preferably ≤about 2% w/w.

"Dry" or "dried" native final forms may refer to compositions with a moisture or water content≤about 70% w/w, preferably ≤about 10% w/w; more preferably ≤about 5% w/w and most preferably ≤about 2% w/w or ≤about 0.5% w/w. Typically, water is undesirable in sterilized finished dried product, especially in the case of gamma irradiation sterilization, because the water promotes actinic induced free radical degradation of organic molecules.

Freeze phase separation or, alternatively, 3-dimensional printing, with carbonic acid chitosan also offers a means to produce novel, shaped scaffold articles. Freeze-drying (sublimation) of the chitosan freeze phase separated chitosan carbonic acid solutions provides for finished dried sponges with substantially no acid content, which do not dissolve under physiologic neutral conditions, and which do not adhere to tissue unless another adhesive agent is added to the chitosan. Such scaffolds infiltrated with different levels of growth factors can be used in tissue engineering soft tissue and hard tissue regeneration applications. For example, such compositions can be used in dental reconstruction, maxillofacial reconstruction, diabetic ulcer tissue regeneration, myocardial tissue regeneration and orthopedic regeneration of bone.

Inclusion of a soluble hydrophilic component in the chitosan matrix to modify the chitosan physical properties, chitosan matrix bioactivity, or to provide for ionic crosslinking may be used. The compositions of the present invention may further comprise additional hydrophilic polymers and/or less hydrophilic polymers. The additional polymer may include, but is not limited to, collagen, collagen derivative, gelatin, alginate, chitosan derivative, keratin, a hydrophilic polyamine, a hydrophilic polyamine salt, polydiallyldimethylammonium salt, polyhexamethylene biguanide, polyaminopropyl biguanide, a chitosan derivative, polylysine, polyethylene imine, xanthan, carrageenan, quaternary ammonium polymer, chondroitin sulfate, a starch, a modified cellulosic polymer, a dextran, hyaluronan, carbopol, polyvinyl pyrrolidone, hydrogenated vegetable oil, paraffin, polyethylene-oxide, polyvinylalcohol, polyvinylacetate, pullulan, pectin or combinations thereof. The starch may include, but is not limited to, amylase, amylopectin and a combination of amylopectin and amylase. The modified cellulosic polymer may include, but is not limited to, ethylcellulose, methycellulose, hydroxypropylcellulose, hydroxypropylmethycellulose, hydroxyethycellulose, carboxymethylcellulose, oxidized cellulose, or combinations thereof.

Inclusion or dissolution of a pharmaceutical or other active agent at a fraction of the chitosan content in the chitosan carbonic acid solution prior to freeze phase separation and freeze-drying provides for localized delivery of the pharmaceutical or active agent from the chitosan material final form. Pharmaceuticals and active agents suitable for use with the present invention, include, without limitation, typical pharmaceuticals that are used in controlled topical delivery including, but are not limited to, antimicrobial, analgesic, antifibrinolytic, and/or growth factors. The compositions of the present invention may further comprise an active ingredient. The active ingredient may include, but is not limited to, calcium, albumin, fibrinogen, thrombin, factor VIIa, factor XIII, thromboxane A2, prostaglandin-2a, activated Protein C, vitronectin, chrondroitin sulfate, heparan sulfate, keratan sulfate, glucosamine, heparin, decorin, biglycan, testican, fibromodulin, lumican, versican, neurocan, aggrecan, perlecan, lysozyme, lysly oxidase, glucose oxidase, hexose oxidase, cholesterol oxidase, galactose oxidase, pyranose oxidase, choline oxidase, pyruvate oxidase, glycollate oxidase and/or aminoacid oxidase, D-glucose, hexose, cholesterol, D-galactose, pyranose, choline, pyruvate, glycollate, aminoacid, epidermal growth factor, platelet derived growth factor, Von Willebrand factor, tumor necrosis factor (TNF), TNF-alpha, transforming growth factor (TGF), TGF-alpha, TGF-beta, insulin like growth factor, fibroblast growth factor (FGF), keratinocyte growth factor, vascular endophelial growth factor (VEGF), nerve growth factor, bone morphogenic protein (BMP), hepatoma derived growth factor (HDGF), interleukin, amphiregulin, retinoic acid, erythropoietin, mafenide acetate, silver sulfadiazine, silver nitrate, nanocrystalline silver, penicillin, ampicillin, methicillin, amoxicillin, clavamox, clavulanic acid, amoxicillin, aztreonam, imipenem, streptomycin, kanamycin, tobramycin, gentamicin, vancomycin, clindamycin, lincomycin, erythromycin, polymyxin, bacitracin, amphotericin, nystatin, rifampicin, tetracycline, doxycycline, chloramphenicol, cefuroxime, cefradine, flucloxacillin, floxacillin, dicloxacillin, potassium clavulanate, clotrimazole, cyclopiroxalomine, terbidifine, ketoconazole, paclitaxel, docetaxel, imatinib, exemestane, tamoxifen, vemurafenib, ipilimumab, dacarbazine, interleukin-2, abiraterone, doxorubicin, 5-fluorouracil, tamoxifen, octreotide, sorafenib, resveratrol, ketamine, diclofenac, ibuprofen, paracetamol, codeine, oxycodone, hydrocodone, dihydromorphine, pethidine, buprenorphine, tramadol, venlafaxine, flupirtine, carbamazepine, gabapentin, pregabalin, lidocaine, autologous cell lines, stem cells, and combinations thereof.

In one embodiment of the present invention, adding a mass fraction of pharmaceutical or other active agent to the chitosan carbonic acid solution and mixing or dispersing it in the solution provides for controlled delivery and release of the pharmaceutical agent by diffusion or dissolution from the chitosan material finished form. It is contemplated that the pharmaceutical or other active agent will be released from the chitosan material finished form by diffusion or dissolution in the presence of biological fluid or when wetted prior to, or following topical application. The rate of release of the active agents from the matrices may be controlled by matrix pore size and interconnectivity, by active agent weak bonding and hydrogen bonding to insoluble matrix polymers, by matrix wettability, by matrix density, by level of matrix dispersion of the active agent, by level of matrix homogeneity of the active agent, and by rates of dissolution of structural and surface polymer layers.

In one embodiment of the present invention, addition of derivatized polycationic chitosans may be used in the chitosan carbonic acid solution at a mass fraction of the chitosan content to provide antibacterial efficacy to the near pH neutral (about pH 7.0) chitosan material finished forms. Such derivatized polycationic chitosans include, but are not limited to, chitosan-arginine and N-trimethyl-chitosan, which are water soluble at physiological pH (7.4).

At the same time, a controlled dissolution element may be used with pharmaceutically active agents for a dissolution mode of controlled delivery.

The present invention includes the following methods and compositions: (1) method of preparing a chitosan carbonic acid solution with substantially no residual salts or contamination; (2) method of preparing a chitosan carbonic acid solution with fibrous reinforcing chitosan residues and with substantially no residual salts or contamination; (3) chitosan material finished forms with substantially no residual salts or contamination, and methods for preparing such finished forms without the requirement for secondary steps of neutralization or extraction of the finished articles; (4) reinforced material finished forms with substantially no residual salts or contamination, and methods for preparing such articles without the requirement for secondary steps of neutralization or extraction of the finished articles; (5) methods of preparing freeze phase separated carbonic acid solution sheets with substantially no residual salts or contamination; (6) chitosan phase separated hydrogel molded finished forms with substantially no residual salts or contamination, and methods for preparing such articles by freeze phase separation without requirement for freeze-drying; (7) chitosan material finished forms containing active pharmaceutical or active agent components with or without additional excipients, and methods for preparing such articles without the requirement for secondary steps of neutralization or extraction of the finished articles; (8) chitosan material finished forms containing a mass fraction of polycationic derivatized chitosan alone or with active pharmaceutical or other active agents, and method for preparing such articles without the requirement for secondary steps of acid neutralization or acid extraction of the finished articles.

BRIEF DESCRIPTION OF THE SEVERAL VIEWS OF THE DRAWINGS

The accompanying Figures, which are incorporated in and constitute a part of this specification, illustrate various exemplary embodiments.

DETAILED DESCRIPTION OF THE INVENTION

Figure 1:
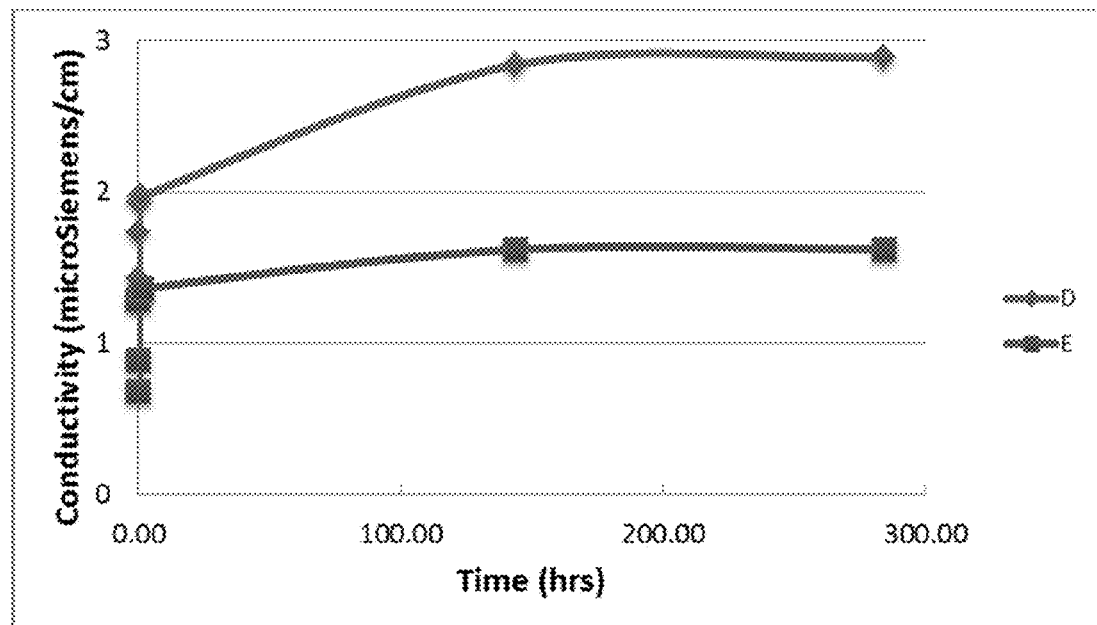
FIG. 1 Provides conductivity measurement of extent of chitosan article D (0.075 g) immersed in deionized water (5.0 g) in closed 15 ml Falcon tube over 300 hours of extraction relative to a control sample E (5.0 g) of deionized water also in a closed 15 ml Falcon tube.

Although the disclosure hereof is detailed and exact to enable those skilled in the art to practice the invention, i.e., to make native chitosan based material final forms, the physical embodiments herein disclosed merely exemplify the invention that may be embodied in other specific structures.

With respect to the Experiments described below, the materials and equipment used are noted as follows, unless otherwise specified with respect to a given Experiment. The water used was deionized water from HemCon's Millipore deionization system. The carbon dioxide was USP Grade Airgas. One chitosan powder used was a "medium molecular weight" (typically number average molecular weight≥100 and ≤350 kda) chitosan from Marinard with a degree of deacetylation (DDA) determined as 88% by Fourier Transform Infrared Spectroscopy (FTIR) method of Miya, M., Iwamoto, R., Yoshikawa, S., and Seiichi, M., *I.R. spectroscopic determination of CONH content in highly deacylated chitosan*, INT. J. BIOL.L MACROMOL., 1980. 2(5), p. 323-324 ("Miya"); and gel permeation chromatography determination of molecular weight as number average molecular weight (Mn)=139 kDa, with polydispersity=2.6 (GPC gel permeation chromatography) standards were National Institute of Standards and Technology (NIST) monodisperse polyethylene oxide Mw standards. The Brookfield Series LVT viscometer measurement at 1% acetic acid and 1% chitosan at 25° C. was >400 cps. Another chitosan powder used was a "low molecular weight chitosan" (typically number average molecular weight≥30 and ≤70 kda) from AKBIOTECH with degree of deacetylation determined as 81% by method of Miya (above). The Brookfield LVT viscometer measurement at 1% acetic acid and 1% chitosan at 25° C. was ≤50 cps. The glacial acetic acid used was from Aldrich. The sodium hydroxide pellets used were supplied from British Drug Houses (BDH) Americal Chemical Society Reagent (ACS).

The deionized water washed nylon mesh strainer bag (near 500 ml) capacity with tripod support was from Fox Run Craftsmen, Ivylands, Pa., 18974 USA. The conductivity measurements were performed using a Thermo Orion 3 Star Conductivity Benchtop system with 5 ml samples being removed for testing. A Gardco AP-99501101 11" Microm II doctors' blade was used for depositing uniformly thick frozen layers (typically 0.25 mm to 5 mm thickness). The freeze-dryer used was a Virtis Genesis 25XL freeze-dryer. Also used were a nebulizer (Mucosal Atomization Device, Wolfe Tory Medical Inc.) and a 20 ml plastic luer lock syringe (HSW) (Henkesasswolf).

Experiment #1: Dry chitosan powder does not dissolve in carbonic acid:

An aqueous dispersion (765 g) at 23±2° C. containing 15 g of Marinard chitosan powder, mechanically stirred with a paddle stirrer at 130 rotations per minute (rpm) in a one liter Ace glass reactor for 24 hours subject to positive pressure (≥1 psi) bubbling of CO2 near 100 ml/min through the dispersion resulted in no noticeable change in the viscosity of the aqueous system or dissolution of the chitosan powder.

About 300 g of the CO2 saturated aqueous dispersion described in the immediately preceding paragraph was placed in CO2, flushed, and CO2 internal pressure was maintained near 60 psi in a one liter flask at room temperature for five days with rolling on roll mill near 20 rpm with no detectable change in the viscosity of the aqueous solution or dissolution of the chitosan powder.

Experiment #2: Preparation of neutralized, washed aqueous chitosan gel particles from a dispersion of medium molecular weight chitosan:

An aqueous dispersion (765 g) (BDH at room temperature, i.e., 23±2° C.) containing 15 g of the medium molecular weight chitosan and 15 g of glacial acetic acid was placed overnight on roll mixer at 40 rpm after which chitosan fully dissolved and formed a viscous clear chitosan acetate solution. The chitosan solution was transferred to a two liter beaker with addition of close to 100 ml of 10M NaOH aqueous solution near 20 ml/minute with mechanical paddle stirring of about 130 rpm. The acidity (pH) of the chitosan solution was monitored with pH paper.

A dense aqueous chitosan precipitate in the form of fine (estimated ≥0.25 mm diameter) hydrated gel particles was observed to form at pH≥10. Also, on addition of the concentrated NaOH to the chitosan solution under the shear of stirring at near 1,000 rpm, the interfacial region between chitosan and the NaOH was observed to induce a precipitated vortex of extended milky-colored fibrous strands ranging in length from about 25 mm to about 1 mm that appeared to eventually, after three to five minutes of mixing, be broken up into smaller pieces about 0.5 mm to about 10 mm by the shear of the mixing. Sodium hydroxide addition was continued with stirring until pH>13.0. Addition was then stopped and system was allowed to sit covered overnight at room temperature. There was some visual evidence of sedimentation of the gels and fibers after 12 hours of precipitation.

Residual chitosan free liquid was decanted and the hydrated, precipitated chitosan gel was collected in the nylon mesh strainer bag to allow further draining of water with retention of the chitosan gel particles and fibers. Securing the open end of the bag and applying local hand gloved pressure placed on the bag near five psi was able to squeeze another 20% w/w water from the closed bag. It is estimated that the remaining mass of the gel particles was at least 90% water. Because dehydrated chitosan is insoluble to carbonic acid, the washed chitosan gel was never allowed to dry between washings. Typically, over 15 washings with water of at least three times the volume of the washed and pressed gel residue were used to rehydrate and wash the gel of residual sodium hydroxide and sodium acetate.

Washings at room temperature involved pouring about one liter of fresh deionized water for each washing over the precipitated chitosan gel and were performed with at least four washings per day over five days. During the washing, the sedimented chitosan gel particles were re-suspended inside the nylon mesh bag by gentle agitation with a paddle. The mesh bag was generally partially submerged in a beaker of fresh water during the addition of the wash water. This submersion in water ensured that the chitosan gel remained hydrated at all times.

It was found that after each wash that the conductivity changed significantly in the early stage of the wash but equilibrated back to near the original conductivity when the system was allowed to sit at room temperature. This indicated that the process of extraction of residual salt from the gel was diffusion limited and that sitting over two-three hours was necessary to achieve equilibration between salt content in the gel and in the washing water. As the conductivity dropped to less than ten microsiemens/cm on washing at room temperature, the time for equilibration increased to the extent that leaving the system to equilibrate overnight achieved the best salt extraction from the gel. This approach allowed an extraction of the gel to below three microsiemens/cm after five days washing at room temperature with longer extraction (>10 days) providing extraction to near about 1 microsiemens/cm: the fresh water at room temperature having conductivity close to about 0.5 microsiemens/cm. According to the Handbook of Chemical Physics, $89^{th}$ Edition, CRC Press, Boca Raton, Fla., 2008, p 5-73, 1.0 microsiemens of sodium hydroxide (originally 2% w/w acetic acid and 5.2% w/w NaOH) indicates a concentration of NaOH at less than 200 parts per billion (ppb) indicating substantial neutralization of basicity [NaOH] as well as removal of ionic salts. The conductivity before washing with 5.2% w/w NaOH according to Handbook of Chemical and Physics was >200,000 microsiemens.

The washing step is typically controlled by determination of the conductivity or pH of final washings in the presence of the chitosan gel for at least 8 hours. In the case of use of pure water in the washing step (not adjusting for physiological electrolyte as described previously) the target conductivity at 23±2° C. for the final washings in the washing step is preferably about ≤50 microsiemens/cm, more preferably about ≤10 microsiemens/cm and most preferably about ≤1 microsiemens/cm. The target pH for the final washings in the washing step is preferably ≥about 5.0 and ≤about 8.5, preferably ≥about 5.5 and ≤about 8.0, more preferably ≥about 6.0 and ≤about 7.5, and most preferably ≥about 6.5 and ≤about 7.0.

Final washed aqueous gel at room temperature maintained a particulate gel-like consistency with gel particles about ≥about 0.25 mm. It had a milky appearance. It was apparent at the end of the washings of the chitosan gel that the dried chitosan was a more white material (less yellow compared to the original) and that there was no detectable odor associated with the washed chitosan indicating removal by washing of more soluble colorant and odoriferous residues of the original chitosan extraction process. Depending on the care in washing the aqueous chitosan particulate inside the mesh bag there was some loss of chitosan during the washing. It is estimated that the yield of chitosan at the end of washing was ≥50% w/w indicating loss of chitosan substantially as fine particulate gel, but also as soluble lower molecular weight residue.

Experiment #3: Preparation of neutralized, washed aqueous chitosan gel particles from a dispersion of low molecular weight chitosan:

Experiment #2 was repeated with the exception that low molecular weight chitosan was used in place of the medium molecular weight chitosan. The outcomes were similar with the number of washings and length of time required to obtain an aqueous gel particle dispersion with low conductivity (<3 microsiemens/cm) and substantially acid salt free being similar. The final aqueous gel particulate diameter in the case of the low molecular weight chitosan was smaller than the medium molecular weight gel particle (≥about 0.1 mm). This difference in size and weight reduced the yield of the washed low molecular weight chitosan compared to the medium molecular weight chitosan. The low molecular weight chitosan also appeared to produce less fibrous strands at the chitosan and NaOH interface during the base induced precipitation of chitosan possibly associated with the lower shear in stirring the substantially less viscous low molecular weight solution. Upon completion of the washings the dried low molecular weight chitosan, like the medium molecular weight chitosan, was a more white (less yellow) material compared to prior to its washing, and there was no detectable odor associated with the washed chitosan.

Experiment #4: Dissolution of the washed gel under the influence of carbonic acid:

The chitosan gel particle washings (250 g) at room temperature of Experiment 2 were purged under CO2, transferred to a cylindrical one liter vessel, and pressurized to 75 pounds per square inch (psi) under carbon dioxide. The vessel was placed on a roll mixer at 40 rpm and at room temperature with its contents allowed to mix overnight. The gel precipitate was found to be dissolved after the overnight mixing. Although the gel solution did not fully clarify under the processing indicating some residual level of insoluble material, there was no visual evidence of particles wetting and sticking to the side of the vessel nor did any sediment settle when left to stand.

Experiment #5: Preparation of freeze phase separated, freeze dried water insoluble pure chitosan sponge native final form:

An aqueous dispersion (1018 g) of the Marinard chitosan powder (18 g) in a one liter cylindrical container was solubilized at room temperature by addition of 20 g of acetic acid and mixing on a roll mixer at 40 rpm and at room temperature overnight. The chitosan solution was transferred to a two liter beaker with addition of close to 100 ml of 10M NaOH aqueous solution near 20 ml/minute with mechanical paddle stirring near 130 rpm for 5 to 10 minutes. The acidity (pH) of the chitosan solution was monitored with pH paper.

As found previously, a dense aqueous chitosan precipitate was observed to form at pH≥10 from the original chitosan solution at room temperature. Also, on addition of the concentrated NaOH to the chitosan solution under the shear of stirring, the interfacial region between chitosan and the NaOH was observed to induce a precipitated vortex of extended milky fibrous chitosan strands ranging in length from about 25 mm to about 1 mm that appeared to eventually be broken up into smaller pieces of about 0.5 mm to about 10 mm by the shear of the mixing. Sodium hydroxide addition was continued with stirring at close to 1,000 rpm until pH was >13. The solution was then washed repeatedly as described in Experiment #2 until the conductivity of the washed precipitate reached a sustained conductivity of 1.05 microsiemens/cm with ≥15 washings of at least three parts water to one part gel over at least 7 days. Water (255 g) at room temperature was added to the washed aqueous chitosan gel concentrate (560 g) and the mixture was transferred to a one liter pressure vessel purged with CO2 and pressurized with CO2 to 45 psi. A thick (≥about 500 cps) milky chitosan solution formed after mixing on a roller mixer at 40 rpm for three days. The CO2 pressure was released and the thick carbonic acid chitosan solution was poured out of the reaction vessel into a two liter beaker with an additional 370 g of carbon dioxide purged water used to rinse the remainder from the pressure vessel. The 1,185 g of carbonic chitosan solution mixture at room temperature was maintained with a CO2 gas head under atmospheric pressure and then 778 g of the mixture was then added back into the one liter pressure vessel with an atmospheric pressure CO2 head and mixed for 30 minutes.

After mixing, 40.14 g of the chitosan carbonic acid solution at room temperature was coated onto the pre-cooled (−40° C.) surface of a Teflon-coated aluminum 10"×20"×0.25" plate with a uniform 3.5 mm gap between the Doctor's blade and the Teflon surface. The chitosan solution frozen onto the aluminum plate was placed in a Virtis freeze-dryer and freeze-dried over 48 hours to a residual water content in the chitosan matrix of about ≤5% w/w. The weight of the dried chitosan sponge was 0.49 g indicating the chitosan solution contained 1.22% chitosan.

A further 180 g of the 1.22% w/w carbonic chitosan solution was frozen onto pre-cooled Teflon coated aluminum 10"×20"×0.25" plates with a uniform 3.5 mm gap between the Doctor's blade and the Teflon surface. The pre-cooled plates (from sitting inside the Virtis lyophilizer shelves at −40° C.) had been placed on a flat polystyrene insulation pad and coated with a uniform thin layer of ice using a nebulizer spray prior to the coating of the chitosan solution. The ice layer was applied to induce a uniform instantaneous base ice nucleation and thus uniform chitosan structure in the phase-separated, freeze-dried chitosan sheet. The plates were replaced in the Virtis lyophilizer and freeze-dried to remove the phase-separated and base ice by sublimation.

Experiment #6: Properties of the freeze phase separated, freeze-dried carbonic acid chitosan solutions:

The resultant freeze-dried chitosan sponge sheets from Experiment #5 were uniformly thick (3.5 mm) with density near 0.012 g/cm3. There was no significant shrinkage (as indicated by less than 5% shrinkage in width and length) and no cracking associated with the casting of sheets near 15" long×9" wide. The sheets demonstrated some mild curling (2" lifting either side) from their middle away from the plates, however this was readily removed by applying a small (1 lb) planar load overnight under conditions of 23±2° C. and 40±5% humidity to the entire sheet surface with the sheet supported on an underlying flat surface. The resultant flat sheets were readily cut into individual 40 mm×40 mm pieces with a sharp razor. The pieces were insoluble when soaked in water at room temperature. They exhibited minimal shrinkage on wetting with water (<10% in length and width). The pieces remained intact after wetting and could be manipulated and moved to different locations on a wet surface without the risk of tearing or fracturing the pieces. The wet pieces conformed intimately in contact with underlying surfaces but did not adhere to them.

By contrast, chitosan 3.5 mm thick sheets which were more conventionally formed directly from acetic acid and 1.8% w/w chitosan solution using the same freeze-phase separation onto plates and freeze-drying, when exposed to water immediately began to dissolve and adhere to the underlying surface. The same 1.8% w/w chitosan solution sheets from acetic acid solution when baked at 130° C. for 20 minutes to substantially remove the acetic acid, became fragile when exposed to water making it impossible to keep a typical dressing piece (4 cm×4 cm) intact when attempting to move it from one wet location to the next.

Conductivity measure of water alone (5 ml) and freeze phase-separated, freeze dried carbonic acid sheet (0.075 g) placed in 5 ml of water in a 15 ml Falcon tube are shown in FIG. 1. It can be seen in FIG. 1 that the water only (E) and chitosan sponge pieces (D) initially at 0.68 and 1.28 microsiemens/cm, respectively, gain conductivity over time with a slightly greater gain in chitosan sponge (1.61 microsiemens/cm) over 300 hrs of soaking compared to the water only (0.94 microsiemens/cm).

Water absorbency at room temperature of the freeze phase-separated, freeze dried sheet from chitosan carbonic acid solution was investigated. At 5 minutes of exposure of 0.0097 g of the sheet to water the amount of water absorbed was 0.13 g (1300%). At 20 minutes the absorbency was 0.14 g (1446%). This absorption of water was achieved with minimal swelling of the sheet (length, width, and height dimensional changes≤about 10%). Such high absorbency and minimal swelling are ideal characteristics of wound dressings. It is contemplated that dressings according to the present invention can be prepared that have a water absorbency capacity of 1000% to 1600% of their dry weight, a water absorbency capacity of between 1200% to 1500% of their dry weight, or a water absorbency capacity of between 1300% to 1450% of their dry weight.

Experiment #7: Formation of native final form intact gel sponge or hydrogel of chitosan freeze/thaw of chitosan carbonic acid solution:

In an attempt of trying to achieve precipitation of the chitosan from the carbonic chitosan solution, 5 ml of the chitosan carbonic solution from Experiment #6 was placed in a capped 15 ml falcon tube at room temperature and then placed overnight in a freezer at −40° C. The next day, on attempting to thaw the chitosan solution, it was found that the solution had formed an insoluble chitosan "hydrogel"

that molded to the shape of the base of the falcon tube. The chitosan "hydrogel" molded plug matching the inner dimensions of the falcon tube with around 5% shrinkage was removed from the falcon tube. It was found to resist light hand pressure (≤0.05 psi) including resistance to deformation and tearing. It could be compressed with moderate hand pressure (≥0.5 psi) like a sponge forcing removal of the water it contained. On immersion in water, it absorbed the water and assumed its original shape. Surprisingly, the chitosan "hydrogel" molded plug would not re-solubilize, i.e., remained insoluble, upon exposure to water or the acid which dissolved the originally neutralized gel.

180 g of the chitosan carbonic acid solution was placed in a 4"×4"×0.8" Teflon coated cavity in an aluminum mold. The mold and its contents were placed in the −40° C. freezer overnight. The mold was then removed from the freezer and the frozen contents allowed to thaw to room temperature. The 180 g of solution had phase separated to a surprisingly insoluble hydrogel chitosan sponge close to 3.8"×3.8"×0.8" that could be physically removed from its cavity and handled without tearing or fracturing the formed hydrogel article. The article was formed close to the exact dimensions of the mold. The "hydrogel" sponge article could be compressed to readily force water from its interstices causing it to lose its shape. It would regain its shape by immersion in water.

Experiment #8: Poly(diallyl dimethyl ammonium chloride) controlled release native final form:

This experiment was performed to evaluate the ability of the carbonic chitosan to release soluble incorporated material over time.

Freeze-dried, freeze phase separated carbonic acid chitosan sheets were prepared near 3.5 mm thickness with poly(diallyl dimethyl ammonium chloride) at 0.0, 2.5% and 10.0% w/w. Elution of poly(diallyl dimethyl ammonium chloride) in 5.0 g of water from 0.05 g pieces of cut chitosan sheet (about 1.5 cm×3.0 cm) was determined using conductivity in 15 ml Falcon tubes over 72 hours.

The materials used included: water—Omnipur WFI quality water, acetic acid (Aldrich), sodium hydroxide (BDH (ACS Reagent)), carbon dioxide (USP Grade Airgas), poly (dially dimethyl ammonium chloride) (Polysciences Mw 8,500 da, 28% w/w in aqueous solution), medium molecular weight chitosan powder from Marinard with degree of deacetylation (DDA) determined as 88% by FTIR method of Miya; and gel permeation chromatography determination of molecular weight as number average molecular weight (Mn)=139 kDa, with polydispersity=2.6 (GPC standards were NIST monodisperse polyethylene oxide Mw standards). The Brookfield LVT viscometer measurement at 1% acetic acid and 1% chitosan at 25° C. was >400 cps.

Chitosan carbonic acid solution 2.0±0.1% w/w was prepared as previously described. In targeting end weight fractions of 10% w/w and 2.5% w/w in the native dried chitosan sheets, poly(diallyl dimethyl ammonium chloride) was mixed into 50±2 g of the 2.0±0.1% chitosan solutions by addition of 357±5 and 89±2 microliters respectively of 28% w/w poly(diallyl dimethyl ammonium chloride) aqueous solution. These solutions were then poured onto 10"×20"×0.25" Teflon coated aluminum plates pre-cooled at −40° C. and adjusted to a thickness near 3.5 mm using the Doctor's blade. The plates with the frozen chitosan coating were then placed onto the freeze-dryer shelves at −40° C., the freeze-dryer was closed, the freezing was continued for another 60 minutes to complete freeze phase-separation of the ice and non-aqueous components. At the completion of the freezing, a freeze-drying cycle was run at 170 mTorr over 16 hours in a Virtis freeze-dryer ramping the shelves quickly from −40° C. to −15° C. and subsequently to 25° C. for final drying. Mass analyses of the final freeze dried samples indicated final moisture≤10% w/w.

Cut pieces (around 15 mm×30 mm×3.5 mm) of freeze dried sheet (0.05±0.005 g) were added to 5.0 g of water and elution of poly(dially dimethyl ammonium chloride) was measured by conductivity (Thermo Orion 3 Star Conductivity Benchtop system) at 0, 5, and 20 minutes and at 1, 3, 8, 24, 32, 48, and 72 hours. Samples were tested in duplicate and pure water was used as a control.

Figure 2:
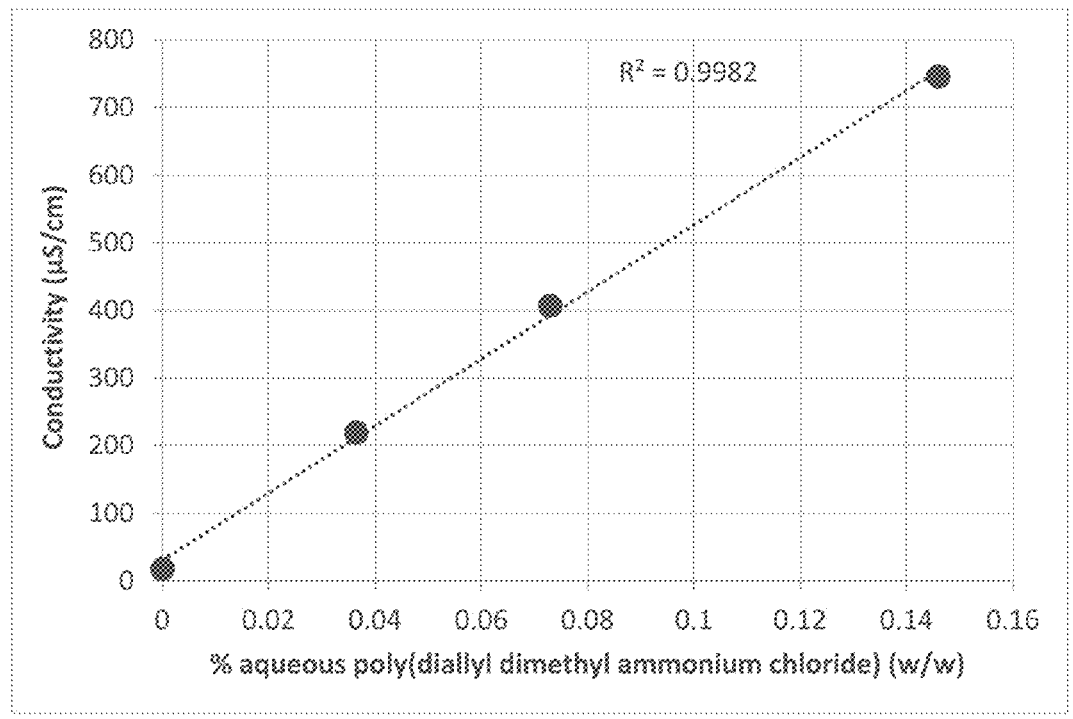
FIG. 2 Demonstrates linearity between Conductivity (10 to 750 microsiemens/cm) of poly(diallyl dimethyl ammonium chloride) aqueous solution and weight fraction of poly(diallyl dimethyl ammonium chloride) (0.0-1,600 ppm) (0.0-0.16% w/w) in solution.
Figure 3:
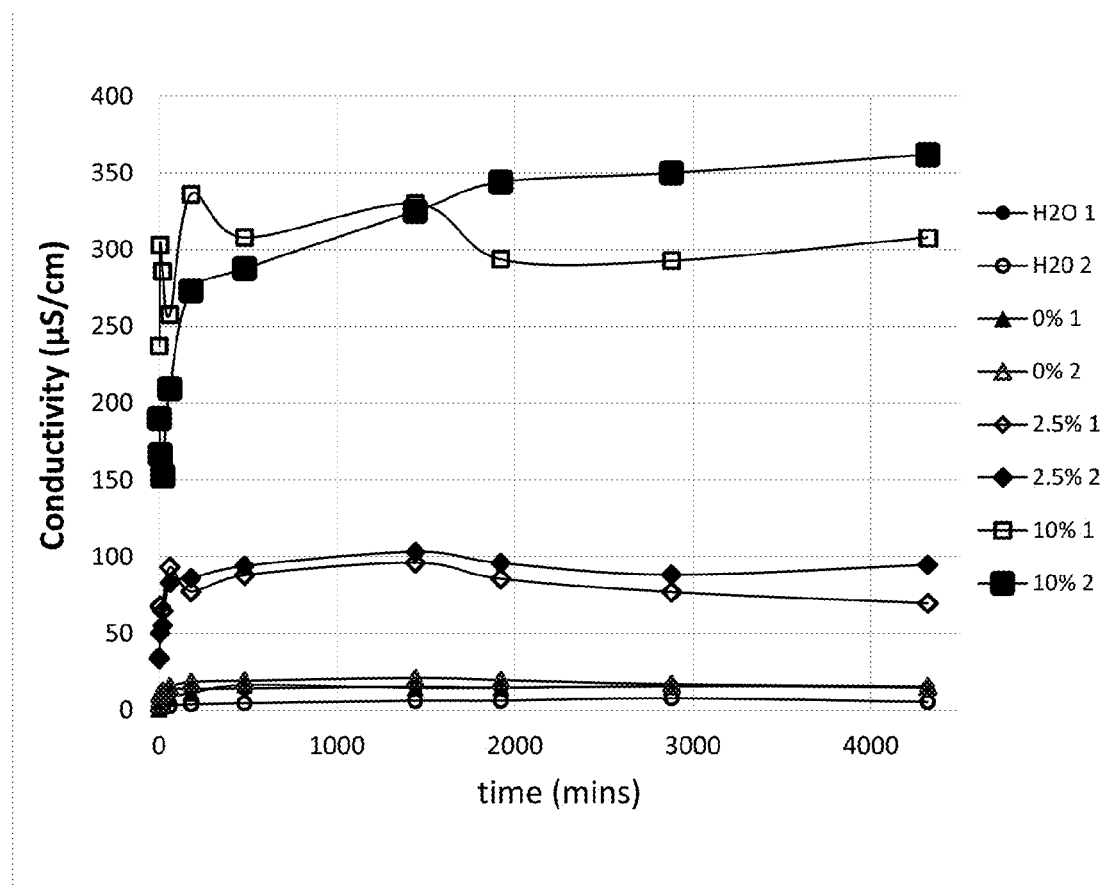
FIG. 3 Demonstrates conductivity profiles in duplicate (indicated 1 & 2) over 4,320 minutes (72 hours) for elution of poly(diallyl dimethyl ammonium chloride) at 100,000 ppm (10.0% w/w), 25,000 ppm (2.5% w/w) and 0.0 ppm (0.0 w/w), in 5.0 g of deionized water (contained in 15 ml Falcon tubes) from 7 days old freeze phase separated and freeze dried carbonic acid chitosan sheets (with and without the polycation near 0.05 g total dry weight and 3.5 mm thickness). Control conductivity of deionized water ($H_2O$) over 4,320 minutes (72 hours) in 15 ml Falcon tubes is included.

Conductivity in FIG. 2 is shown to be directly proportional to concentration of the poly(diallyl dimethyl ammonium chloride). FIG. 3 demonstrates rapid release of the poly(diallyl dimethyl ammonium chloride) from the wetted chitosan matrix within the first 120 minutes followed by more gradual release over the next 72 hours. The chitosan Sheets with 0% poly(diallyl dimethyl ammonium chloride) are close to indistinguishable (FIG. 3) from water in their conductivity elution profile demonstrating that there is substantially no residual acid salt in the freeze-dried chitosan.

These results further support that native chitosan finished articles formed from carbonic acid chitosan solution can be used to deliver and release substances such as poly(diallyl dimethyl ammonium chloride) in a manner which is suitable for active substance delivery.

Figure 7:
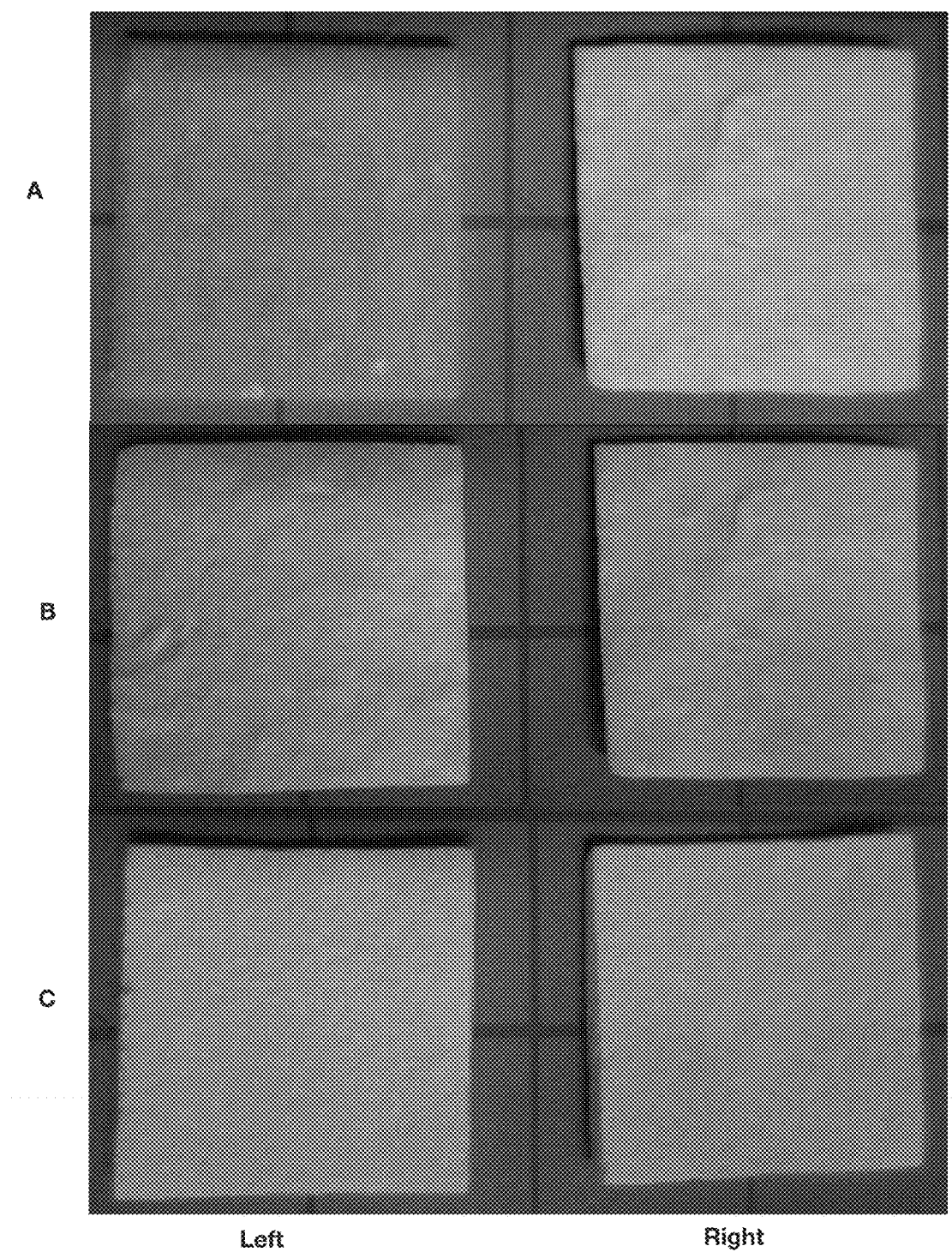
FIG. 7 Black & white digital photo images of 40 mm×40 mm×3.5 mm freeze phase separated 100.0% w/w chitosan, freeze-dried sheets: A) comparison of chitosan acetate (left) and carbonic acid chitosan (right) identically freeze phase-separated, freeze dried prepared sheets; B) top surface view of freeze phase separated 100.0% w/w chitosan, freeze dried sheets; and C) aluminum plate base layer view of freeze phase separated 100.0% w/w chitosan, freeze dried sheets.

Experiment #9: Controlled release of chitosan-arginine native final form:

Finished carbonic acid chitosan freeze phase-separated and freeze dried materials were prepared with the Marinard chitosan (described in example 8) and 0.0 ppm (0.0% w/w), 5,000 ppm (0.5% w/w), 25,000 ppm (2.5% w/w), and 100,000 ppm (10.0% w/w) of chitosan-arginine. The synthesis of chitosan-arginine, an antimicrobial agent, has been described by Lee et al. See Lee, J., Duncan, A., Townsend, S., and Baker, S., *Synthesis and characterization of a chitosan derivative* (976.3), THE FASEB JOURNAL, 2014, 28(1 Supplement) ("Lee"). Dressing sheets were prepared from the carbonic acid solutions of chitosan premixed with adjusted % w/w chitosan-arginine solutions to form uniform frozen 3.5 mm thickness thin layer sheets (close to 25 cm×18 cm) of the solutions on pre-cooled, ice-coated plates at −45° C., and subsequently removing the ice by freeze-drying the composition to a final moisture content of ≤about 5% w/w. The fractional chitosan-arginine fractional compositions of 0.0%, 0.5%, 2.5% and 10.0% w/w were in the finished dry sheets with respective 100.0%, 99.5%, 97.5%, and 90% w/w of pure chitosan substantially free of acid salts. FIG. 7 provides photo images, right-hand column images A, B, and C, of the 4 cm×4 cm cut 100.0% chitosan dressings; the left-hand column images provide photo images of a similarly prepared sheet, but directly from dilute acetic acid solution. The dressing sheets were cut into 4 cm×4 cm dressing pieces for testing with dressing weights between 0.072 and 0.085 g. The basis weight of the dressings was near 45 g/cm2. The dressings demonstrated similar wet handling and absorbency properties as described in Experiment #6.

The elution profile of the chitosan-arginine from the dressings was readily determined by wetting the dressings with excess deionized water and measuring conductivity resulting from the concentration of chitosan-arginine released from the dressing into the deionized water. The chitosan-arginine elution from the dressings was determined in duplicate for chitosan-arginine loadings of 100,000, 25,000, 5,000, and 0 ppm at three months storage (23±2° C.), at 100,000 at 25,000 ppm at 12 months storage (23±2°

C.) and at 100,000 and 25,000 ppm at 12 months storage (23±2° C.) with exposure to gamma irradiation of 14 to 17.2 kGy 11 months after dressing preparation. Storage was inside sealed Kapak™ polyethylene packaging for all dressings.

Figure 4:
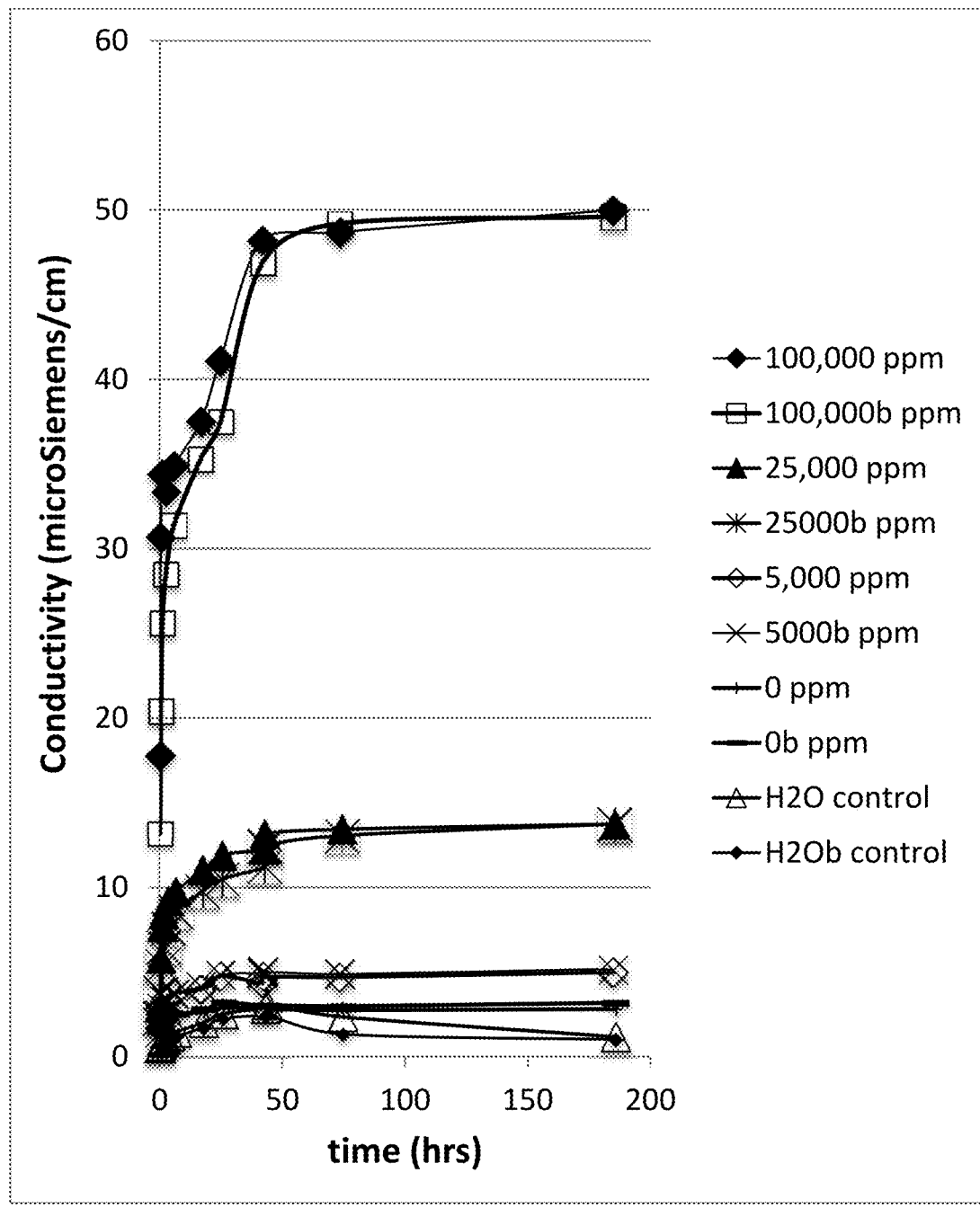
FIG. 4 Demonstrates conductivity profiles in duplicate over 186 hours for elution of chitosan-arginine at 100,000 ppm (10.0% w/w), 25,000 ppm (2.5% w/w), 5,000 ppm (0.5% w/w) and 0.0 ppm (0.0 w/w) from 3 month storage (23±2° C., ≤5% w/w moisture) freeze phase separated and freeze dried carbonic acid chitosan sheets (0.072 to 0.085 g dry weight) 40 mm×40 mm×3.5 mm thickness in 5.0 g of deionized water contained in 15 ml Falcon tubes. Control conductivity of deionized water in 15 ml Falcon tubes is included.
Figure 5:
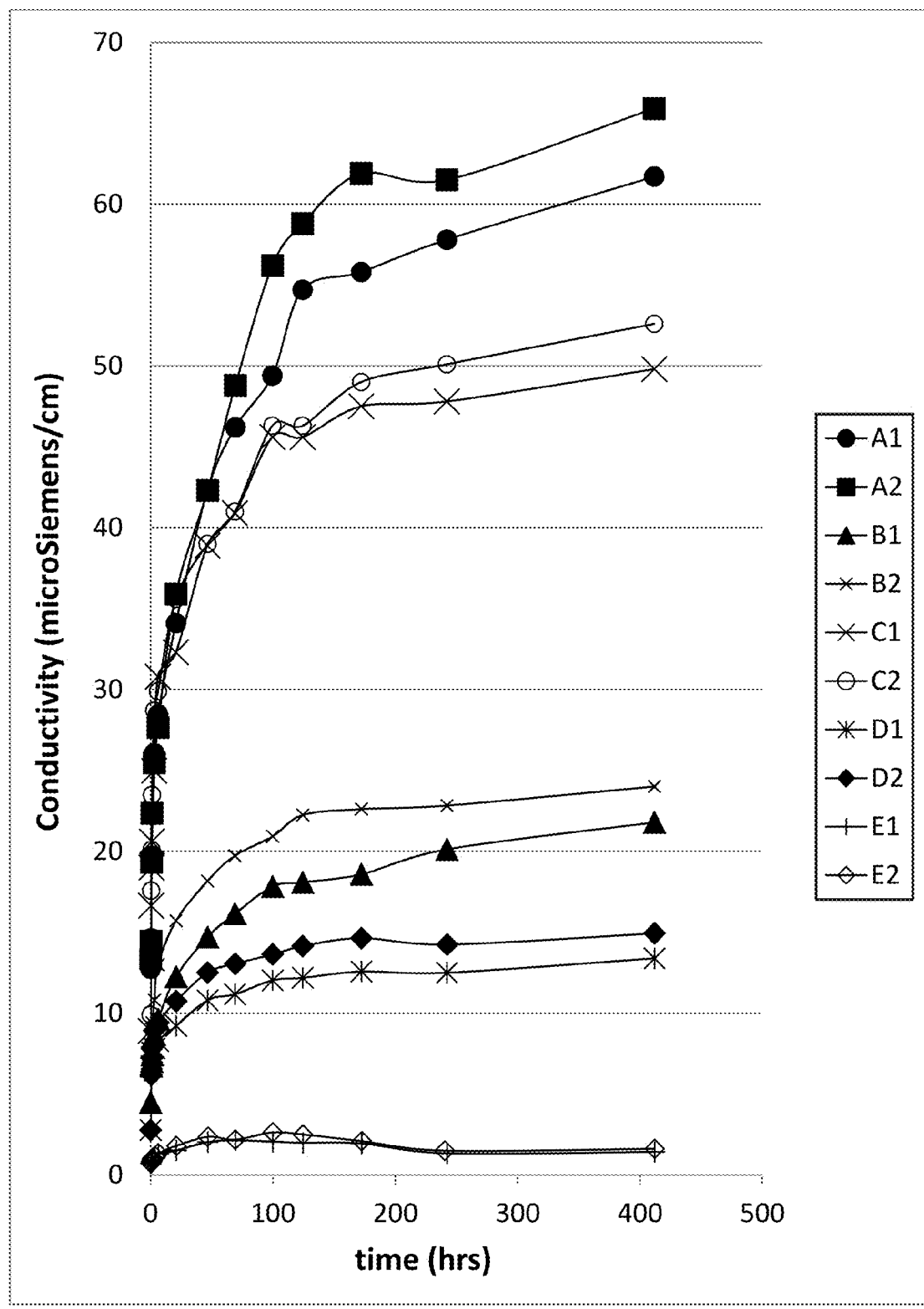
FIG. 5 Demonstrates elution profiles in duplicate over 420 hours of conductivity for 40 mm×40 mm×3.5 mm chitosan dressings (0.072 to 0.085 g dry weight) at 12 months storage (23±2° C.) with 100,000 ppm (10.0% w/w) chitosan-arginine loaded gamma-irradiated dressings (A1, A2); 100,000 ppm (10.0% w/w) chitosan-arginine loaded not gamma-irradiated dressings (C1, C2); 25,000 ppm (2.5% w/w) chitosan-arginine loaded gamma-irradiated dressings (B1, B2); 25,000 ppm (2.5% w/w) chitosan-arginine loaded not gamma-irradiated dressings (D1, D2); and controls (E1, E2) of no dressing in same 5.0 ml of H20 in and same capped 15 ml polypropylene Falcon tube as dressing samples.

The aqueous elution characteristics in 5.0 g of deionized water (0.5 microsiemens/cm) of the chitosan-arginine from individual dressings after 3 and 12 months storage at room temperature are demonstrated in FIGS. 4 and 5. It can be seen in FIG. 5 that conductivity (i.e. amount of chitosan-arginine released) is increased by gamma irradiation exposure.

In the case of the non-irradiated dressing loaded to 25,000 ppm, it can be seen that 3 month and 12 months elution profiles (FIGS. 4 and 5) are very similar. Interestingly for the non-irradiated dressing loaded to 100,000 ppm elution profiles at 3 months and at 12 months, the elution profiles are very similar with the same three stages of i) initial rapid release of chitosan-arginine to conductivity near 30 microsiemens/cm in 6 hours or less; ii) transition after release of the first 30 microsiemens/cm to a slower steady rate of release until reaching conductivity near 50 microsiemens/cm at 50 hours (three month age) and 100 hours (12 months age); and iii) after reaching 50 microsiemens/cm there is a much reduced apparent long term asymtopic release of chitosan-arginine to around 55 microsiemens/cm.

Surprisingly, after gamma irradiation in both 25,000 ppm and 100,000 ppm chitosan-arginine loaded dressings, there is substantial conductivity and elution rate increases in stages ii) and iii) in the 100,000 ppm loaded samples and there is appearance of the same type of stages in the 25,000 ppm loaded samples with similar increases caused by gamma irradiation. A preliminary hypothesis for the cause of this gamma-irradiation conductivity increase would be that the gamma irradiation is promoting macromolecular scission and, thus, releasing lower molecular weight chitosan-arginine and chitosan matrix with lower coefficients of diffusion.

A control chitosan matrix without any chitosan-arginine was not included in this initial gamma irradiation series. Inclusion of such a control would be desirable in any future work to eliminate the possibility of gamma irradiation producing charged chitosan fragments that could confound interpretation of conductivity change.

Figure 6:
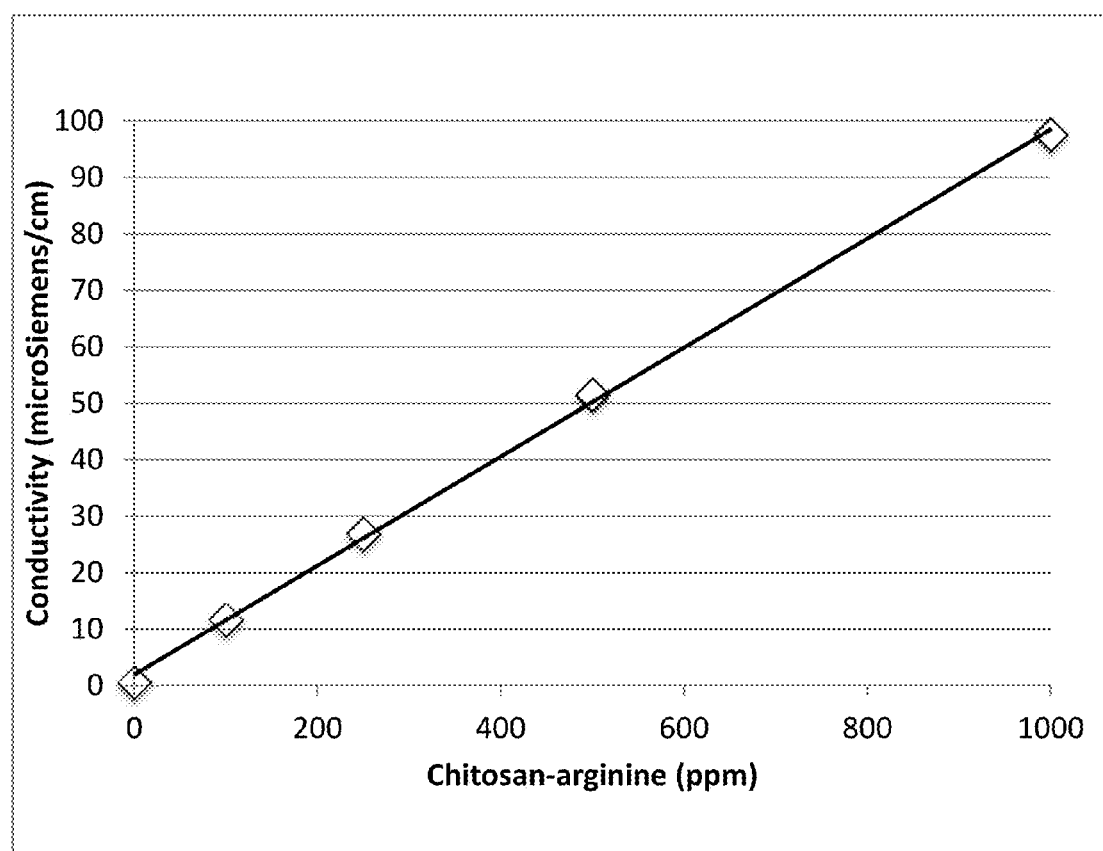
FIG. 6 Linearity between conductivity and concentration of chitosan-arginine in water ($y=1.92\pm0.83+0.0966\pm0.0016x$, $R^2=0.999$, where y is conductivity μS/cm and x is chitosan-arginine concentration in ppm).

FIG. 6 demonstrates linearity between conductivity and concentration of the chitosan-arginine in water ($y=1.92\pm0.83+0.0966\pm0.0016x$, $R^2=0.999$, where y is conductivity μS/cm and x is chitosan-arginine concentration in ppm). In the absence of confounding effects, this linear correlation between chitosan-arginine concentration in water and its conductivity may be used to determine concentration of chitosan-arginine by measurement of conductivity.

The results of this preliminary stability analysis provide confidence that delivery of chitosan-arginine from a native solid final form freeze-dried chitosan matrix as an antibacterial treatment is very likely efficacious, safe and resilient to effects of gamma-irradiation sterilization and shelf life effects (two to three years at 25° C.) with storage in moderately protective packaging expected for use in a short term delivery (1 to 7 days) controlled release device. It is anticipated that further shelf life studies may be undertaken to demonstrate stability in final packaging of a locked prototype.

In summary, the present invention includes a promising chitosan material dressing that provides controlled release of the antimicrobial agent, chitosan-arginine. Three concentration loadings (5,000 ppm, 25,000 ppm, 100,000 ppm) of chitosan-arginine dressings have been developed, the 25,000 and 100,000 ppm concentrations have a high likelihood of demonstrating antibacterial and wound healing efficacy in a large animal model.

The invention claimed is:

1. A solid or semi-solid native final form composition comprising uniformly dispersed chitosan fibers within a substantially acid salt free chitosan solubilized gel material, wherein said material is incapable of repeated solubilization in a carbonic acid aqueous solution having a pH between about 3.4 to about 7.0.

2. The composition of claim 1, wherein the final form composition comprises one of a powder, fiber, film, matrix, sponge, implant, scaffold, filler, and hydrogel and has an acid salt content of between about 0.01% (w/w) and about 5% (w/w).

3. The composition of claim 1, wherein the final form composition includes a controlled release pharmaceutical or active agent delivery vehicle.

4. The composition of claim 1, wherein the final form composition is non-adhesive, remains intact upon exposure to water, saline, blood or other biological fluid, and can remain on wounds or wet tissue surfaces over four to seven days without significant change.

5. The composition of claim 1, wherein the substantially acid salt free chitosan solubilized gel material comprises one of medium weight and low weight chitosan.

6. The composition of claim 1, wherein the final form composition is a water insoluble freeze phase molded hydrogel.

7. The composition of claim 1, wherein the final form composition comprises water in an amount of less than about 10% (w/w).

8. The composition of claim 7, wherein the final form composition absorbs between about 1000% and 1600% of water based on its weight (w/w).

9. The composition of claim 1, wherein the final form composition has a density of about 0.005 to 0.25 g/cm$^3$.

10. The composition of claim 1, wherein the final form composition has a density of about 0.12 g/cm$^3$.

11. The composition of claim 1, wherein the final form composition does not require acid salt elution.

12. The composition of claim 1, wherein the final form composition comprises a freeze-dried sponge.

* * * * *